United States Patent
Riedmann et al.

(10) Patent No.: US 7,446,322 B2
(45) Date of Patent: Nov. 4, 2008

(54) METHOD AND DEVICE FOR RECOGNIZING DARK STATES DURING THE SPECTROSCOPIC OR MICROSCOPIC EXAMINATION OF FLUORESCENT SPECIMENS

(75) Inventors: Juergen Riedmann, Obersulm-Eschenau (DE); Werner Knebel, Kronau (DE); Lioba Kuschel, Mannheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 90 days.

(21) Appl. No.: 11/358,591

(22) Filed: Feb. 21, 2006

(65) Prior Publication Data
US 2006/0186345 A1  Aug. 24, 2006

Related U.S. Application Data

(60) Provisional application No. 60/758,303, filed on Jan. 12, 2006.

(30) Foreign Application Priority Data
Feb. 22, 2005  (DE)  ........................ 10 2005 008 196

(51) Int. Cl.
*F21V 9/16* (2006.01)

(52) U.S. Cl. .................................................. 250/459.1

(58) Field of Classification Search ............. 250/459.1, 250/458.1, 461.1, 461.2, 462.1
See application file for complete search history.

(56) References Cited

U.S. PATENT DOCUMENTS

| | | | | |
|---|---|---|---|---|
| 5,185,265 | A * | 2/1993 | Steen et al. ..................... 436/63 |
| 5,602,412 | A * | 2/1997 | Suzuki et al. ................ 257/432 |
| 5,742,437 | A * | 4/1998 | Eguchi et al. ................ 359/739 |
| 5,987,924 | A * | 11/1999 | Lee et al. ....................... 65/102 |
| 6,310,841 | B1 * | 10/2001 | Chung et al. .............. 369/44.24 |
| 6,483,582 | B2 * | 11/2002 | Modlin et al. ................ 356/317 |
| 6,954,306 | B2 * | 10/2005 | Engelhardt ................... 359/381 |
| 2002/0036824 | A1 * | 3/2002 | Sasaki ......................... 359/385 |
| 2003/0086067 | A1 * | 5/2003 | Gerstner et al. ................ 353/30 |
| 2004/0099813 | A1 * | 5/2004 | Eggeling et al. .......... 250/459.1 |
| 2004/0264353 | A1 * | 12/2004 | Kitahara et al. ......... 369/112.23 |

FOREIGN PATENT DOCUMENTS

WO   WO 9828646 A1 *  7/1998

* cited by examiner

*Primary Examiner*—Constantine Hannaher
*Assistant Examiner*—Kiho Kim
(74) *Attorney, Agent, or Firm*—Darby & Darby

(57) ABSTRACT

A method for recognizing dark states during the spectroscopic or microscopic examination of fluorescent specimens includes varying an intensity distribution of excitation light by varying an excitation/illumination volume over a plurality of mutually independent measurements. A determination is made as to whether observed time constants change between the measurements. The existence of a dark state is inferred where the observed time constants are unchanged between the measurements.

28 Claims, 2 Drawing Sheets

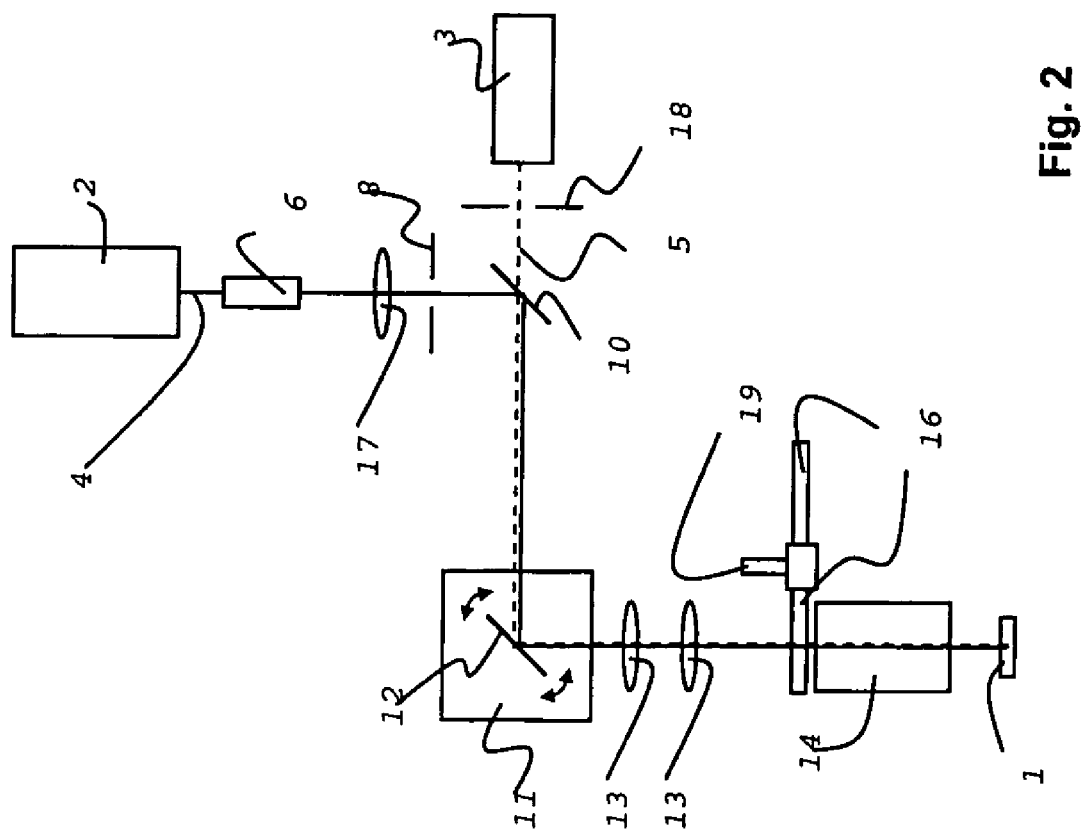

METHOD AND DEVICE FOR RECOGNIZING DARK STATES DURING THE SPECTROSCOPIC OR MICROSCOPIC EXAMINATION OF FLUORESCENT SPECIMENS

Priority is claimed to the U.S. Application 60/758,303, filed by applicants on Jan. 12, 2006, and to German patent application DE 10 2005 008 196.7, filed on Feb. 22, 2005, the entire subject matters of both of which are hereby incorporated by reference herein.

The present invention relates to a method for recognizing dark states during the spectroscopic or microscopic examination of fluorescent specimens, in particular using fluorescent proteins. The present invention also relates to a device for spectroscopically or microscopically examining fluorescent specimens, in particular using fluorescent proteins, including a light source and a detector device, an illumination beam path extending between the light source and the specimen, and a detection beam path extending between the specimen and the detector device.

BACKGROUND

The present invention generally concerns spectroscopic or microscopic examinations which are directed to determining the photochemical properties of observable fluorophores. With respect to relevant, related art publications, reference is made merely exemplarily to U.S. Pat. No. 5,742,437, specifically to column 9, lines 27 through 50, as well as to FIGS. 5 and 14 of the publication.

When biological specimens are examined, it is often living cells that are being observed. Fluorescent proteins are used for fluorescently tagging the cellular proteins of interest using genetic technology. Such a tagging process makes it possible to observe and analyze the protein mobility in the living cell.

What is problematic in this context is a very special phenomenon of the fluorophores, namely the occurrence of so-called dark states. This phenomenon is also called blinking and is caused, for example, by triplet transitions, isomerization, protonation, etc. The occurrence and/or frequency of such dark states, as well as their lifetimes, are dependent on numerous factors, thus, for example, on the environment of the fluorophore, but also, in particular, on the intensity of the excitation light.

The dark states, which occur regularly during observation of biological specimens, cause serious problems when their time constants are within the regions of the diffusion times, making it impossible to still distinguish between the two phenomena. In other words, it is indistinguishable whether the observed state is a dark state or the result of a cell diffusion that has occurred.

SUMMARY OF THE INVENTION

In light of the above explanations, it is an object of the present invention is to provide a method for recognizing dark states during the spectroscopic or microscopic examination of fluorescent specimens, which will make it possible to differentiate between the phenomena to be observed and the dark states which occur. It is also an object of the present invention to provide a device for spectroscopically or microscopically examining fluorescent specimens which, while avoiding the aforementioned problems, is suited for examining biological specimens, in particular using fluorescent proteins.

The present invention provides a method for recognizing dark states during the spectroscopic or microscopic examination of fluorescent specimens using, for example, fluorescent proteins. The excitation/illumination volume, thus the intensity distribution of the excitation light, is varied over the course of at least two mutually independent measurements. A determination is made as to whether the time constants observed in the process change. In the case of unchanged time constants, the existence of a dark state is inferred. Thus, a differentiation is possible.

The present invention also provides a device for spectroscopically or microscopically examining fluorescent specimens using, for example, fluorescent proteins. The device includes a light source and a detector, an illumination beam path extending between the light source and the specimen, and a detection beam path extending between the specimen and the detector, and may be used for implementing a method according to the present invention. The excitation/illumination volume, thus the intensity distribution of the excitation light, is varied over the course of at least two mutually independent measurements, a determination being made as to whether the observed time constants change and, in the case of unchanged time constants, the existence of a dark state being inferred.

The present invention is based on the realization that, for example, genetically tagged cellular proteins have a longer residence time in the region of an illuminating beam having a larger excitation/observation volume than in a "thinner" beam. Accordingly, when two consecutive measurements are taken first under a smaller excitation/illumination volume and, then, under a larger excitation/illumination volume, and the observation does not change, it may, at any rate, be concluded that no diffusion is taking place. In such a case, a dark state is quite obviously recognized. On the other hand, if the observation changes, in the example selected here, diffusion may be inferred, since the changes in the observations are due to different residence times in the illumination volume. If, namely, in response to an increased excitation/observation volume, i.e., an increased confocal illumination volume, the observed time constant also increases in the context of the confocal spectroscopy or microscopy, then the process in question, i.e., the recognized process, is diffusion. On the other hand, however, if the time constant remains the same, there is, namely, no change in the observation, then it is a matter of an intrinsic property, i.e., of a dark state of the fluorophores that are used.

In the method according to the present invention at least two mutually independent measurements be performed under varied excitation/illumination volumes. The method is qualitatively improved by performing a plurality of mutually independent, preferably consecutive measurements, each time under varied excitation/illumination volumes, to ensure greater certainty with regard to the conclusion drawn from the measurements. At any rate, a variation in the excitation/illumination volume induces a change in the residence time of fluorescent proteins in the illuminated region, making it possible for conclusions to be drawn regarding the observed phenomenon.

Thus, the excitation/illumination volume is able to be influenced by varying the aperture, the excitation/illumination volume behaving inversely proportionally to the aperture. The smaller the aperture or the smaller the aperture setting, the greater is the excitation/illumination volume, it being fundamentally a question of the intensity distribution in the focus or in the vicinity of the focus.

Specifically, the excitation/illumination volume is able to be varied by using a preferably variably adjustable pinhole diaphragm in the illumination beam path, the use of an iris diaphragm upstream of the main beam splitter or upstream of an AOBS (acousto-optical beam splitter) being suited. At this location, the light beam should be at least substantially parallel and not be overly large in diameter.

Alternatively, it is conceivable for the excitation/illumination volume to be varied by using a color-selective diaphragm in the illumination beam path, the color-selective diaphragm preferably being placed in the pupil of the objective lens. Moreover, this diaphragm advantageously acts exclusively on the illuminating light, thereby making it possible to vary the illumination of the pupil. It is important in this context that the detection light propagating back from the specimen always pass through the diaphragm, unhindered, to ensure that the signal coming from the specimen is not reduced. Thus, it is conceivable that the diaphragm be designed, for example, for two or more different wavelength regions or wavelengths in such a way that it yields different illumination diameters or illumination patterns for the different wavelengths or wavelength regions. The illumination light "cut off" by the diaphragm is either absorbed in the diaphragm or reflected by the diaphragm and subsequently filtered out of the detection beam path using suitable means. A diaphragm configuration is conceivable, whereby a plurality of diaphragms are mounted on a filter wheel, for example, the diaphragm desired in a particular case being rotatable by the filter wheel into the beam path. It is important in any case that the diaphragm be devised in such a way that the detection light or the emission light propagating back from the specimen not be reduced, since, namely, the photons coming from the specimen are needed for the measurement, i.e., for the correlation sought.

The device according to the present invention for spectroscopically or microscopically examining fluorescent specimens, in particular using fluorescent proteins, including a light source and a detector device, an illumination beam path extending between the light source and the specimen, and a detection beam path extending between the specimen and the detector device, is used, in particular, for implementing the method described above. The device is characterized in that the excitation/illumination volume, thus the intensity distribution of the excitation light, is varied over the course of at least two mutually independent measurements, a determination being made as to whether the observed time constants change and, in the case of unchanged time constants, the existence of a dark state being inferred.

As just explained in connection with the advantageous embodiments of the method according to the present invention, to vary the excitation/illumination volume, a preferably variable pinhole diaphragm, namely an iris diaphragm, for example, may be provided in the illumination beam path. In this respect, it is advantageous when the pinhole diaphragm is positioned in a region of the illumination beam path where the light is at least substantially parallel and, to be precise, preferably upstream of a main beam splitter or an AOBS.

Alternatively, to vary the excitation/illumination volume, provision is made in the illumination beam path for a color-selective diaphragm that is preferably positioned in the pupil of the objective lens. The process of selecting a suitable diaphragm is facilitated by the provision of a plurality of color-selective diaphragms, the plurality of color-selective diaphragms being mounted on one filter wheel and selectively rotatable into the beam path.

The color-selective diaphragm may be used, for example, to allow passage of two different excitation wavelengths, depending on the diaphragm design, the different excitation wavelengths producing different excitation/illumination volumes. The diaphragm is partially transmitting, or semitransparent, in the direction of the illuminating light, i.e., toward the specimen, and it is fully transmitting, or transparent, in the direction of the detection light, i.e., toward the detector device, to allow a sufficient number of photons to impinge on the detector device.

With regard to the advantageous embodiment of the device according to the present invention, it is noted at this point that the diaphragm is advantageously designed to absorb the illuminating light that does not pass through the same. It is also conceivable that the illuminating light that does not pass through the diaphragm is reflected by the same and is completely filtered out of the detection beam path, namely by employing appropriate measures, such as suitable light traps or the like.

BRIEF DESCRIPTION OF THE DRAWINGS

The teaching of the present invention can be embodied and refined in different ways. The present invention is elaborated upon below based on exemplary embodiments with reference to the drawings. In the drawings.

FIG. 2: shows, in a schematic view, a second exemplary embodiment of a device according to the present invention for recognizing dark states during the spectroscopic or microscopic examination of fluorescent specimens; and FIG. 2a illustrates, in a schematic plan view, a color-selective diaphragm for two excitation wavelengths, the two exemplary embodiments being described to clarify the method according to the present invention.

DETAILED DESCRIPTION

Figure 1:
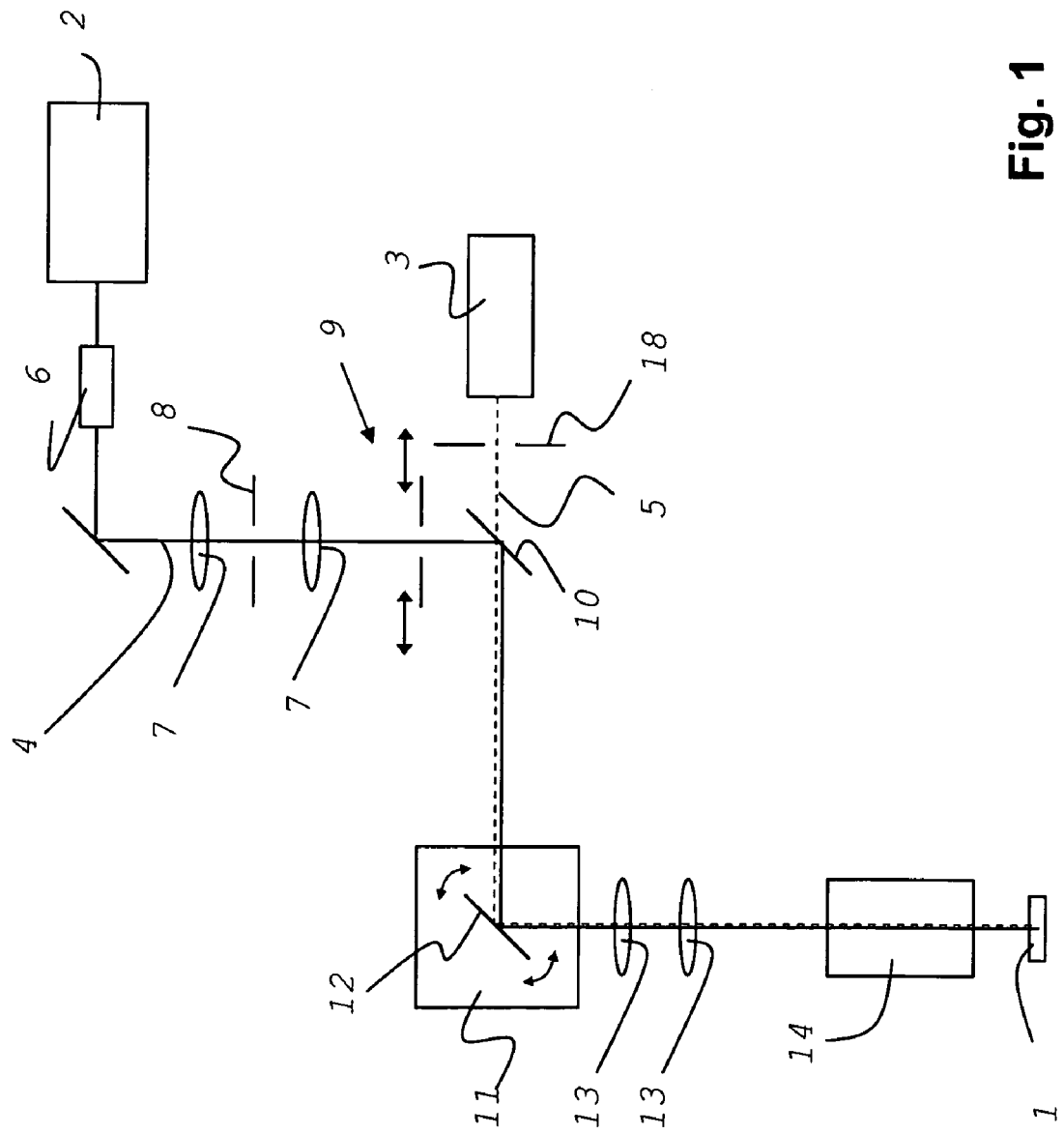
FIG. 1: shows, in a schematic view, a first exemplary embodiment of a device according to the present invention for recognizing dark states during the spectroscopic or microscopic examination of fluorescent specimens.

FIG. 1 shows a first exemplary embodiment of a device according to the present invention for microscopically examining fluorescent specimens 1, these specimens 1 being doped with fluorophores, namely containing fluorescent proteins. The device essentially includes a light source 2, specifically a laser light source. In addition, the device includes a detector device 3. An illumination beam path 4 extends between light source 2 and specimen 1. A detection beam path 5 extends between specimen 1 and detector device 3.

Disposed downstream of light source 2 in illumination beam path 4 is an AOTF (acousto-optical tunable filter) 6 which is used to control the light intensity. After passing through a lens array 7 and an illumination pinhole 8 positioned between the lenses, the illuminating light arrives via an adjustable iris diaphragm 9 at main beam splitter 10, from where it is transmitted via scanning device 11 having scanning mirror 12 and via a lens array 13 through objective lens 14 to impinge on specimen 1.

In the exemplary embodiment illustrated in FIG. 1, the excitation/illumination volume, thus the intensity distribution of the excitation light, is influenced and varied by adjustable iris diaphragm 9, so that, over the course of at least two mutually independent measurements under varied excitation/illumination volumes, a determination is made as to whether the observed time constants change. In the case of unchanged time constants, the existence of a dark state may be inferred, as already described in detail in the general part of the description.

FIG. 2 shows a second exemplary embodiment of a device according to the present invention, a color-selective diaphragm 16 or a plurality of color-selective diaphragms 16 being provided for varying the excitation/illumination volume. In the exemplary embodiment illustrated in FIG. 2, positioned immediately downstream of light source 2 in illumination beam path 4 is an AOTF 6 for adapting the luminous flux. Disposed downstream of a lens 17 is an illumination pinhole 8. The illuminating light is transmitted via main beam splitter 10 to scanning device 11 having scanning mirror 12 and via a lens array 13 through objective lens 14 to specimen 1.

The detection light propagating back from specimen 1 is transmitted via detection beam path 5 through main beam splitter 10 and detection pinhole 18 to impinge on detector device 3, comparably to the exemplary embodiment in accordance with FIG. 1.

A filter wheel 19 having a plurality of color-selective diaphragms 16 is positioned in the pupil of objective lens 14, color-selective diaphragms 16 being movable into the particular working position by rotating filter wheel 19.

Finally, FIG. 2a shows an example of a color-selective diaphragm 16, such as the one located on filter wheel 19 provided in the exemplary embodiment in FIG. 2. Color-selective diaphragm 16 illustrated schematically in FIG. 2a is designed for two different excitation wavelengths. Diaphragm 16 is transparent to the detection light over its entire surface.

With regard to other features that are not inferable from the figures, to avoid repetitive descriptions, reference is made to the general part of the specification.

Finally, it should be noted that the exemplary embodiments discussed above are merely intended for purposes of exemplifying the claimed teaching, but not for limiting it to such embodiments.

What is claimed is:

1. A method for recognizing dark states during the spectroscopic or microscopic examination of fluorescent specimens, the method comprising:
   varying an intensity distribution of excitation light by varying an excitation/illumination volume over a plurality of mutually independent measurements; and
   determining whether respective time constants change between the measurements, and inferring an existence of a dark state where the respective time constants are unchanged between the measurements.

2. The method as recited in claim 1 wherein the fluorescent specimens include a fluorescent protein.

3. The method as recited in claim 1 wherein the measurements are consecutive measurements.

4. The method as recited in claim 1 wherein the varying the excitation/illumination volume is performed by varying an aperture so as to vary the excitation/illumination volume inversely proportionally to the aperture.

5. The method as recited in claim 1 wherein the varying the excitation/illumination volume is performed using a pinhole diaphragm disposed in an illumination beam path.

6. The method as recited in claim 5 wherein the pinhole diaphragm is variably adjustable.

7. The method as recited in claim 5 wherein the pinhole diaphragm includes an iris diaphragm upstream of at least one of a main beam splitter and an acousto-optical beam splitter.

8. The method as recited in claim 1 wherein the varying the excitation/illumination volume is performed using a color-selective diaphragm disposed in an illumination beam path.

9. The method as recited in claim 8 wherein the color-selective diaphragm is disposed in a pupil of an objective lens.

10. The method as recited in claim 1 wherein the measurements are performed under a same light intensity of the excitation light.

11. The method as recited in claim 1 further comprising adjusting, in response to a change in a light intensity resulting from the varying the excitation/illumination volume, the light intensity using an acousto-optical tunable filter.

12. The method as recited in claim 11 wherein the adjusting is performed so as to maintain the light intensity substantially constant.

13. A device for spectroscopically or microscopically examining fluorescent specimens, the device including:
   a light source configured to produce excitation light;
   a detector;
   an illumination beam path extending between the light source and a specimen; a detection beam path extending between a specimen and the detector;
   an excitation/illumination volume variation device configured to vary an intensity distribution of the excitation light by varying an excitation/illumination volume over a source of a plurality of mutually independent measurements; and
   a time constant measurement device configured to measure respective time constants so as to enable a determination of whether the measured respective time constants change between the measurements and an inferring of an existence of a dark state where the measured respective time constants are unchanged between the measurements.

14. The device as recited in claim 13 wherein the specimen includes a fluorescent protein.

15. The device as recited in claim 13 wherein the excitation/illumination volume variation device includes a pinhole diaphragm disposed in the illumination beam path.

16. The device as recited in claim 15 wherein the pinhole diaphragm is variable.

17. The device as recited in claim 15 wherein the pinhole diaphragm includes an adjustable iris diaphragm.

18. The device as recited in claim 15 wherein the pinhole diaphragm is disposed in a region of the illumination beam path where a light beam of the excitation light is at least substantially parallel.

19. The device as recited in claim 15 further comprising at least one of a main beam splitter and an acousto-optical beam splitter, the pinhole diaphragm being disposed upstream thereof.

20. The device as recited in claim 13 wherein the excitation/illumination volume variation device includes at least one color-selective diaphragm disposed in the illumination beam path.

21. The device as recited in claim 20 further comprising an objective lens, and wherein the at least one color-selective diaphragm is disposed in a pupil of the objective lens.

22. The device as recited in claim 21 wherein the at least one color-selective diaphragm includes a plurality of selectable color-selective diaphragms disposed on a filter wheel and selectively rotatable into the illumination beam path.

23. The device as recited in claim 20 wherein the at least one color-selective diaphragm is configured, as a function of a wavelength of the excitation light, to be partially transmitting in a direction toward the specimen and fully transmitting in a direction toward the detector.

24. The device as recited in claim 23 wherein the at least one color-selective diaphragm is configured to absorb light of the excitation light not transmitted by the diaphragm.

25. The device as recited in claim 23 wherein the at least one color-selective diaphragm is configured to reflect and filter out of the detection beam path excitation light not transmitted by the diaphragm.

26. The device as recited in claim 20 wherein the at least one color-selective diaphragm is configured to provide respective illuminating diameters as a function of a wavelength of the excitation light.

27. The device as recited in claim 26 wherein the at least one color-selective diaphragm is configured to absorb light of the excitation light not transmitted by the diaphragm.

28. The device as recited in claim 26 wherein the at least one color-selective diaphragm is configured to reflect and filter out of the detection beam path excitation light not transmitted by the diaphragm.

* * * * *